United States Patent
Haney et al.

(10) Patent No.: US 9,248,407 B2
(45) Date of Patent: Feb. 2, 2016

(54) DIALYSIS DEVICE

(75) Inventors: Paul Jeffrey Haney, Beloit, WI (US); Jeffery James Frank Gordon, Muskegon, MI (US); Brendan George Metz, Plainfield, IL (US); Navid R. Haghdoost, Rockford, IL (US)

(73) Assignee: Pierce Biotechnology, Inc., Rockford, IL (US)

( * ) Notice: Subject to any disclaimer, the term of this patent is extended or adjusted under 35 U.S.C. 154(b) by 545 days.

(21) Appl. No.: 13/618,876

(22) Filed: Sep. 14, 2012

(65) Prior Publication Data
US 2014/0076811 A1     Mar. 20, 2014

(51) Int. Cl.
*B01D 61/28* (2006.01)
*B01D 61/24* (2006.01)
*G01N 1/40* (2006.01)

(52) U.S. Cl.
CPC ............. *B01D 61/243* (2013.01); *B01D 61/28* (2013.01); *G01N 1/4005* (2013.01); *B01D 2313/04* (2013.01); *G01N 2001/4016* (2013.01)

(58) Field of Classification Search
CPC .. B01D 61/28; B01D 2313/04; B01D 61/243; G01N 1/4005; G01N 2001/4016
USPC ......... 210/644, 645, 646, 232, 321.6, 321.75, 210/321.84, 470, 471, 495, 498
See application file for complete search history.

(56) References Cited

U.S. PATENT DOCUMENTS

| | | | |
|---|---|---|---|
| 1,757,364 A | 3/1930 | Heibig | |
| 1,777,057 A | 9/1930 | Urbain | |
| 2,758,083 A | 8/1956 | Van Hoek et al. | |
| 3,459,176 A | 8/1969 | Leonard | |
| 3,679,059 A | 7/1972 | Wyatt et al. | |
| 3,696,931 A | 10/1972 | Hough | |
| 3,804,258 A | 4/1974 | Okiniewski et al. | |
| 4,187,893 A | 2/1980 | Bujan | |
| 4,323,455 A | 4/1982 | Tanaka et al. | |
| 4,419,237 A | 12/1983 | Esmond | |
| 4,597,868 A | 7/1986 | Watanabe | |
| 4,721,555 A | 1/1988 | Grosshandler | |
| 4,828,706 A | 5/1989 | Eddleman | |
| 4,865,813 A | 9/1989 | Leon | |
| 5,085,753 A | 2/1992 | Sherman | |
| 5,185,048 A | 2/1993 | Guerif | |
| 5,324,428 A | 6/1994 | Flaherty et al. | |

(Continued)

FOREIGN PATENT DOCUMENTS

| | | |
|---|---|---|
| DE | 2039050 | 2/1972 |
| EP | 0402611 | 12/1990 |

(Continued)

OTHER PUBLICATIONS

"Dialyzers," Harvard Apparatus Catalog, p. N36 (2004).
European Search Report and Opinion for EP 09 15 2257, mailed May 18, 2009 (7 pages).
International Search Report of the International Searching Authority for PCT/US2005/007609, dated May 19, 2005 (5 pages).
International Preliminary Report on Patentability of the International Searching Authority for PCT/US2005/007609, issued Sep. 13, 2006 (9 pages).
Search Report, GB1314469.6, Feb. 3, 2014 (4 pages).

*Primary Examiner* — John Kim
(74) *Attorney, Agent, or Firm* — Thompson Hine LLP

(57) ABSTRACT

A dialysis device, and a method of dialyzing a sample, are provided. The dialysis device includes a body having a first and a second major side, a first and a second retaining ring disposed on the first and second major sides, and a first and second dialysis membrane disposed, and held between the first and second major sides and the first and second retaining rings. The dialysis device is configured to receive a sample to enable dialysis of the sample across the membranes.

20 Claims, 14 Drawing Sheets

(56) References Cited

U.S. PATENT DOCUMENTS

| | | |
|---|---|---|
| 5,342,517 A | 8/1994 | Kopf |
| 5,503,741 A | 4/1996 | Clark |
| 5,783,075 A | 7/1998 | Eddleman et al. |
| 6,039,871 A | 3/2000 | Sykaluk |
| 6,086,770 A | 7/2000 | Matkovich |
| 6,245,056 B1 | 6/2001 | Walker et al. |
| 6,368,509 B1 | 4/2002 | Bansal et al. |
| 6,531,061 B1 | 3/2003 | Cholewa |
| 7,056,440 B2 | 6/2006 | Haney et al. |
| 8,007,668 B2 | 8/2011 | Haney et al. |
| 2003/0133846 A1 | 7/2003 | Ben-Asouli et al. |
| 2005/0092666 A1 | 5/2005 | Wilson |
| 2009/0200225 A1 | 8/2009 | Haney et al. |

FOREIGN PATENT DOCUMENTS

| | | |
|---|---|---|
| EP | 2 497 506 A1 | 9/2012 |
| EP | 2 671 599 A1 | 12/2013 |
| JP | 2011072814 A | 4/2011 |
| WO | 95/08385 | 3/1995 |
| WO | 2004/089442 A1 | 10/2004 |
| WO | 2005/087353 | 9/2005 |

DIALYSIS DEVICE

A device for the dialysis of samples, such as those commonly dialyzed in the research laboratory, is provided. The device offers convenience in loading and unloading of sample, particularly larger sample sizes.

Figure 1:
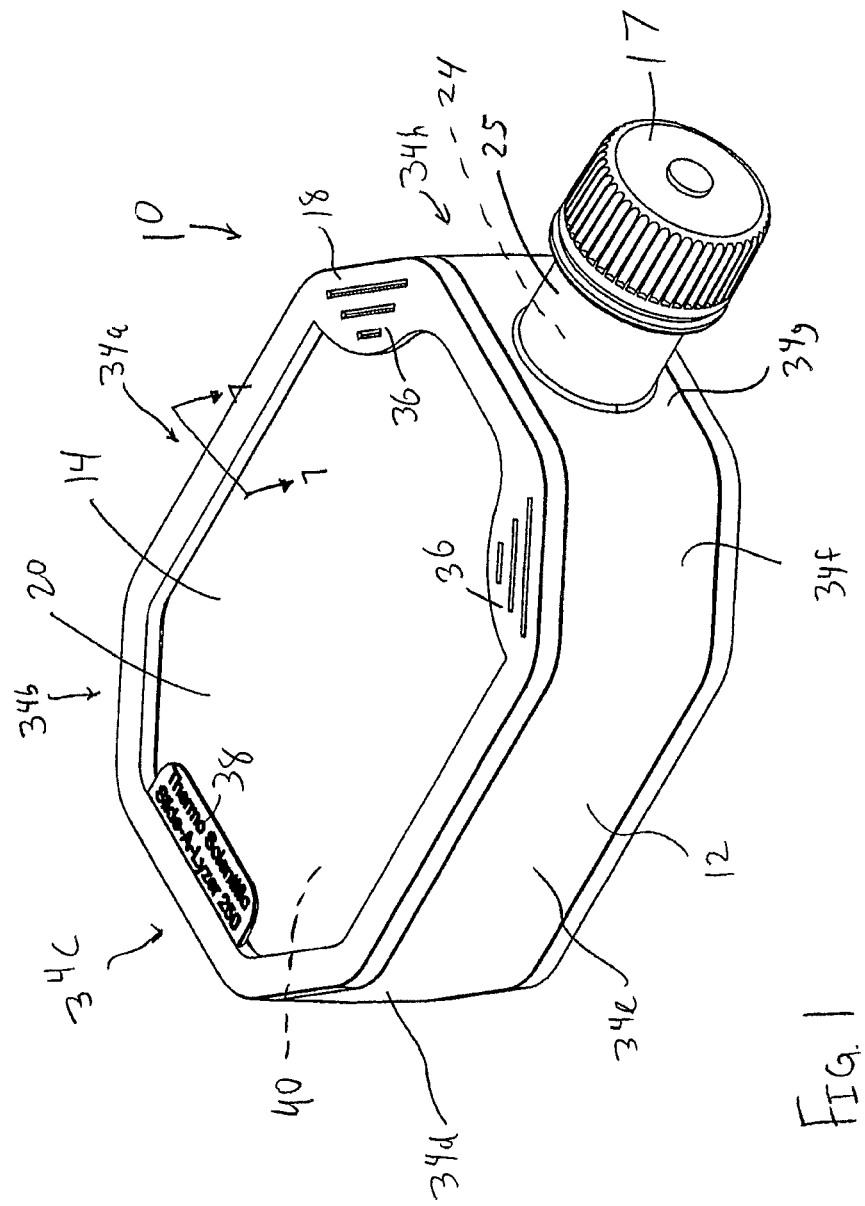
FIG. 1 is a perspective view of one embodiment of a dialysis device.
Figure 2:
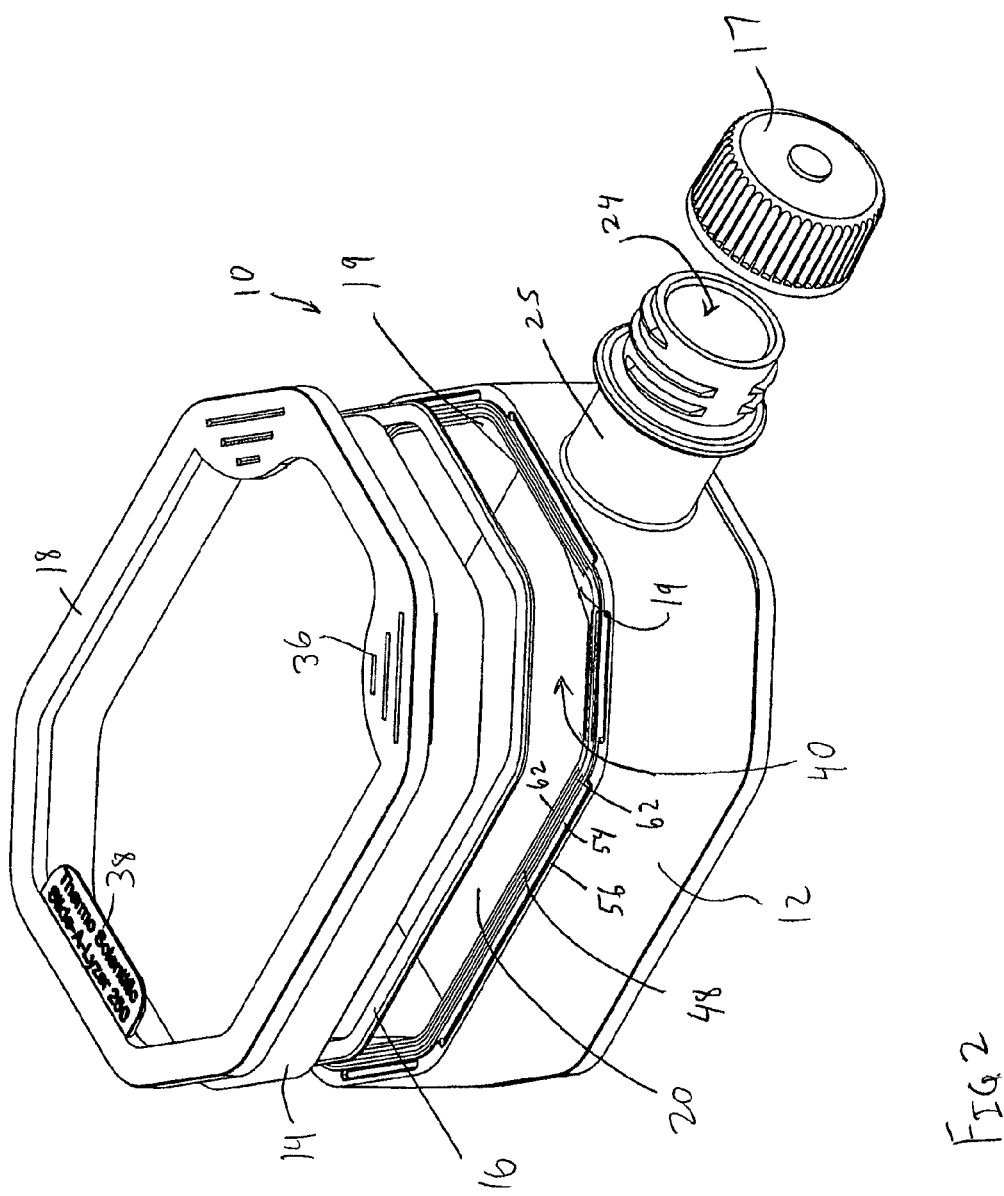
FIG. 2 is an exploded perspective view of the device of FIG. 1.
Figure 3:
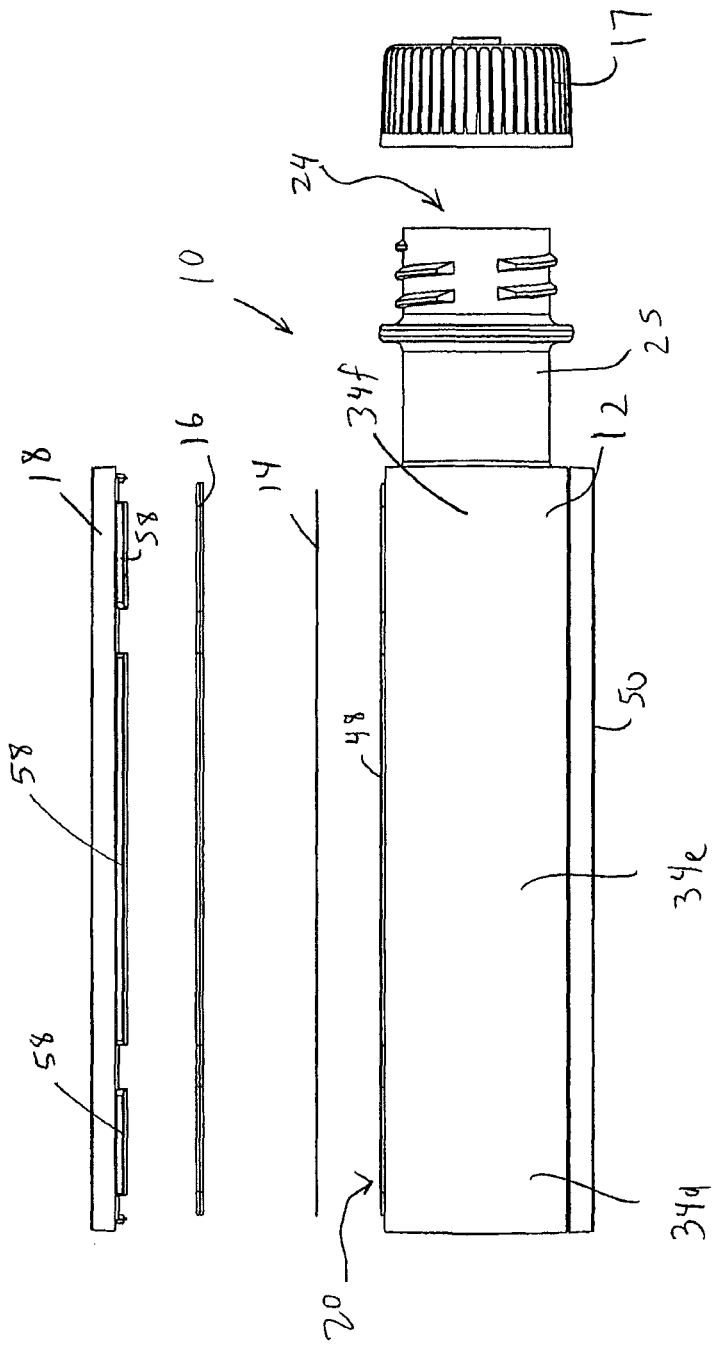
FIG. 3 is an alternate exploded side view of the device of FIG. 1.

In one embodiment, as shown in FIGS. 1-3, the dialysis device 10 includes a body 12, and a pair of dialysis membranes 14, a pair of gaskets 16, and a pair of a retaining rings 18 positioned on opposite sides of the body 12 (it should be understood that only one membrane 14, gasket 16 and retaining ring 18 are shown, on the top side in FIGS. 1-3, but another membrane 14, gasket 16 and retaining ring 18 can be positioned on the bottom side thereof). The body 12 is shown as an extruded component having a generally octagonal shape in top view but can be any of a wide variety of shapes. The body 12 can be made from any of a wide variety of materials, including materials that exhibit a low absorbency of proteins, are substantially rigid, and can survive common sterilization procedures, including but not limited to acrylonitrile butadiene styrene (ABS) or polypropylene. The body 12 has or defines a first major planar side or opening 20, a second major opposed planar side or opening 22 (FIG. 4), and in the illustrated embodiment, has eight generally planar end surfaces 34a, 34b, 34c, 34d, 34e, 34f, 34g and 34f defining an outer perimeter of the body 12. In the illustrated embodiment each end surface 34 is oriented generally perpendicular to the major sides 20, 22. End surface 34c provides the bottom of the dialysis device 10/body 12 when the dialysis device 10 is in a vertical position.

The first major side 20 and second major side 22 of the body 12 may each be generally open (e.g. the sides 20, 22 can be considered to define openings in the body 12), but each is covered by an associated membrane 14 when the dialysis device 10 is assembled. In the assembled form, each membrane 14 is tightly held in a sealed manner between the body 12 and an associated retaining ring 18. The gasket(s) 16 are optional, but when used a gasket 16 can be positioned between the body 12 and the associated retaining ring 18. Each gasket 16 can be positioned between the associated membrane 14 and the body 12 (FIG. 2) or between the with the associated membrane 14 and retaining ring 18 (FIG. 3). Alternately, two gaskets 16 can be utilized, one on each side of the membrane 14.

Figure 4:
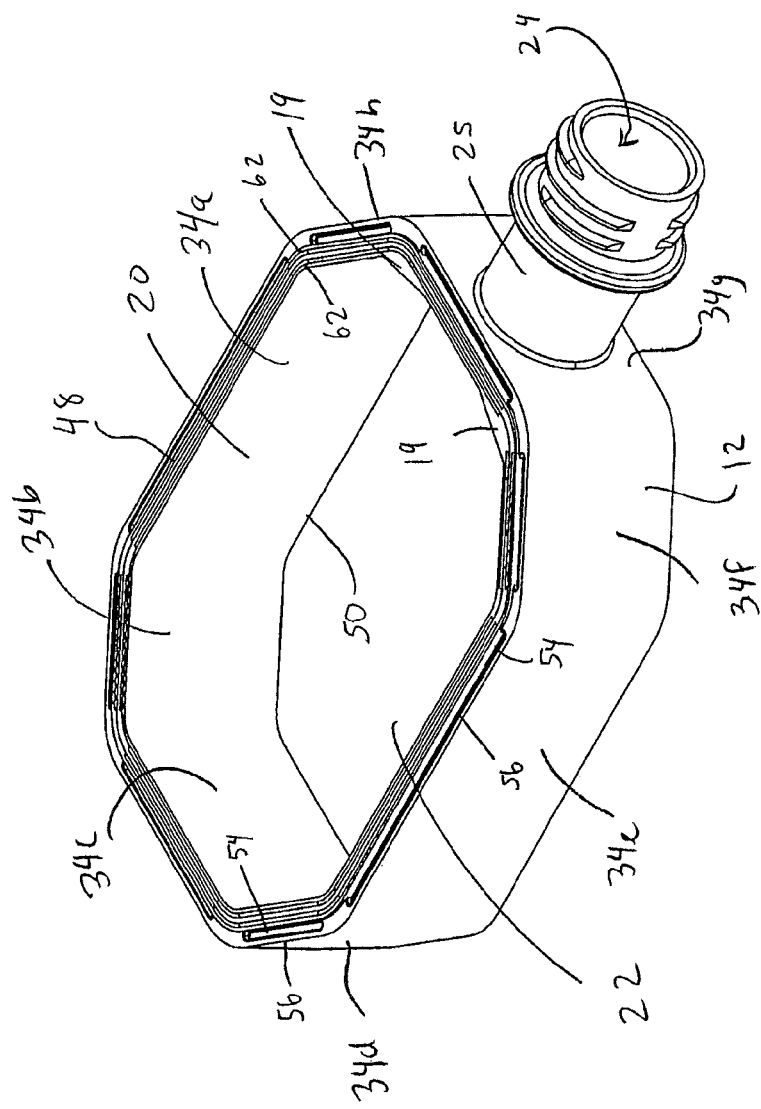
FIG. 4 is a perspective view of the body of the dialysis device of FIG. 2.

The body 12 may have or define an interior volume 40 thereof. In one embodiment, the interior volume 40 has a volume/capacity of between about 75 ml and about 250 ml, although the capacity can be varied as desired. The body 12 may have a neck 25 defining an access opening 24 therein, which is in fluid communication with the interior volume 40, allowing entry and removal of a fluid sample into and from the interior volume 40/dialysis device 10. In one embodiment, the neck 25 has a substantially cylindrical configuration and is joined to the body 12 at end surface 34g. A closure device, such as a cap 17, can be configured to be secured to, and close/seal, the access opening 24 of the neck 25. As shown in FIGS. 2 and 4, the body 12 may include a tapered surface 19 on/inside the end surface 34g to guide fluid into the access opening 24 of the neck 25, when it is desired to pour fluid out of the body 12.

As shown in FIG. 4, one edge of the end surfaces 34 of the body 12 forms or defines a first peripheral edge 48, and the other edge of the end surfaces 34 forms or defines a second peripheral edge 50. The first and second peripheral edges 48, 50 comprise features which engage and/or interact with the membrane 14, the gasket 16, and/or the retaining ring 18, as will be described in greater detail below.

Figure 5:
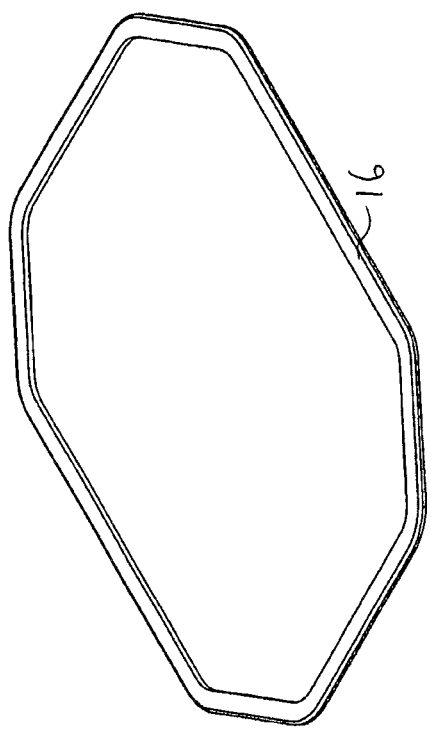
FIG. 5 is a perspective view of the gasket of the dialysis device of FIG. 2.

With reference to FIG. 5, each gasket 16 can have a shape which generally matches the overall shape of the first 48 and/or second 50 peripheral edge. Each gasket 16 can be made of a generally flexible, deformable or pliable material, including but not limited to silicon. With reference to FIGS. 2 and 3, each membrane 14 can be generally flat and planar, having a shape generally corresponding to the first 48 and/or second 50 peripheral edge, although the membrane 14 can have any of a wide variety of shapes and sizes. Each membrane 14 can be made of any of a variety of materials suitable for use in dialysis. In particular, each membrane 14 may be a semi-permeable membrane which allows sufficiently small molecules to pass therethrough, but blocks larger molecules from passing therethrough. In one embodiment, each membrane 14 is made of regenerated cellulose, or cellulose acetate or collagen, but could also or instead be made of other materials.

Figure 6:
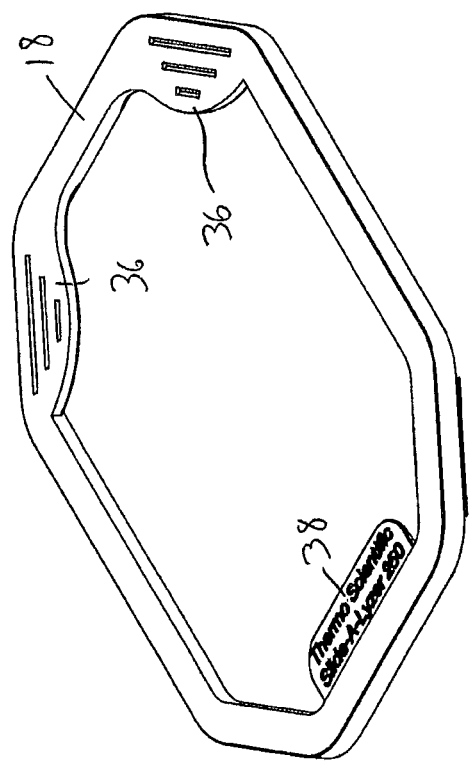
FIG. 6 is a perspective view of the retaining ring of the dialysis device of FIG. 2.

As shown in FIG. 6, each retaining ring 18 has a shape generally corresponding to the shape of the first 48 and/or second 50 peripheral edge. Each retaining ring 18 comprises features which engage and/or interact with the body 12, the associated membrane 14, and/or the associated gasket 16, as described in detail below. In the illustrated embodiment, each gasket 16 is a discrete, separate component. However, if desired each gasket 16 can be integrally formed with a retaining ring 18 and/or the body 12, such as by overmolding in one case. Moreover, in one case only a single dialysis membrane 14, gasket 16 and retaining ring 18 may be utilized, on a single side of the body 12. In this case the opposite side of the body 12 may lack an opening, or the opposite side of the body 12 may include an opening with a membrane 14 secured in a different manner.

As indicated above, corresponding features on the body 12 and retaining ring 18 facilitate engagement and subsequent attachment of each retaining ring 18 with the body 12, along with the associated membrane 14 and optional gasket 16.

Various embodiments of these engagement features are shown in FIGS. 7-14. In describing the various engagement features, reference will be made to the components of one of the major sides 20, 22 of the dialysis device 10. However, it should be understood that such descriptions can apply equally to the other major side 20, 22 of the dialysis device 10. Nevertheless the features of one of the major sides 20, 22 need not necessarily be the same features found on the other major side 20, 22.

Figure 7:
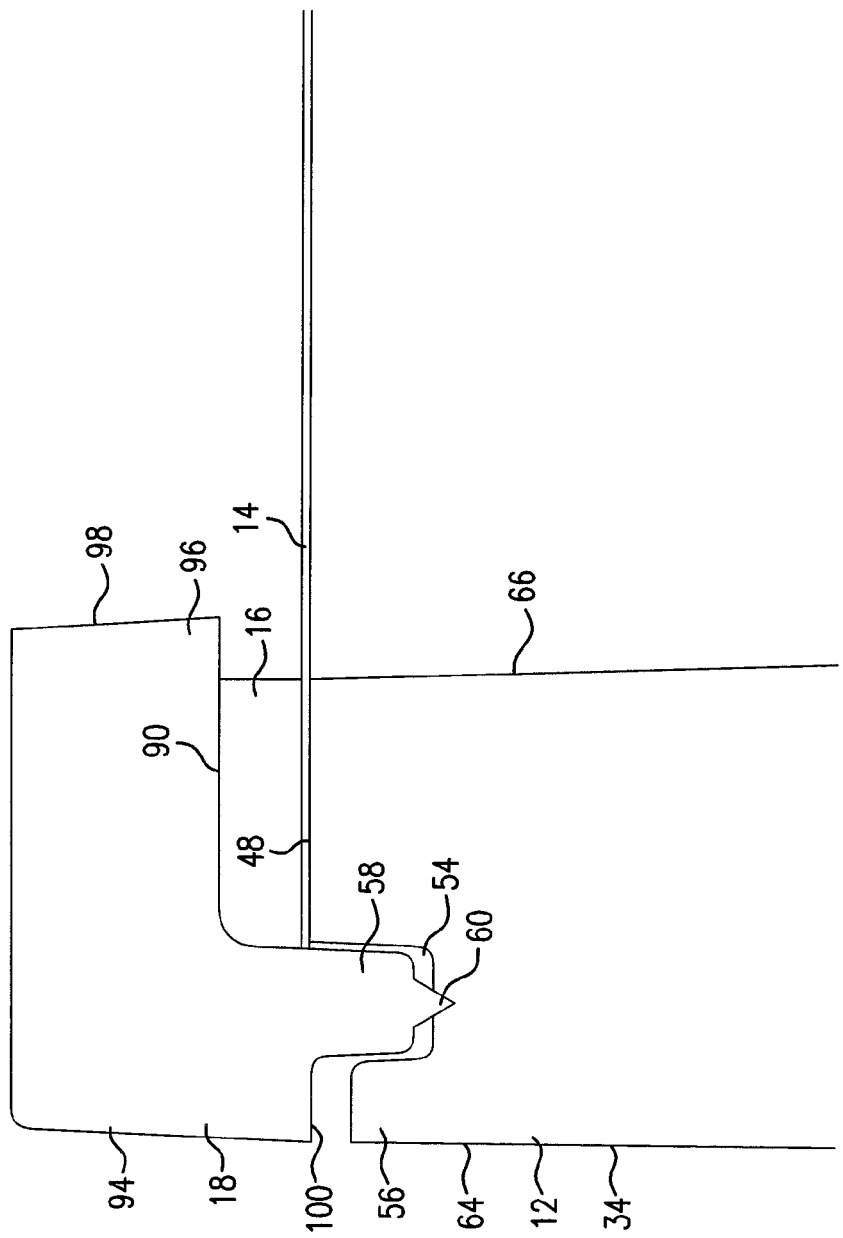
FIG. 7 is a side partial cross section of one embodiment of the dialysis device, taken along line 7-7 of FIG. 1.
Figure 8:
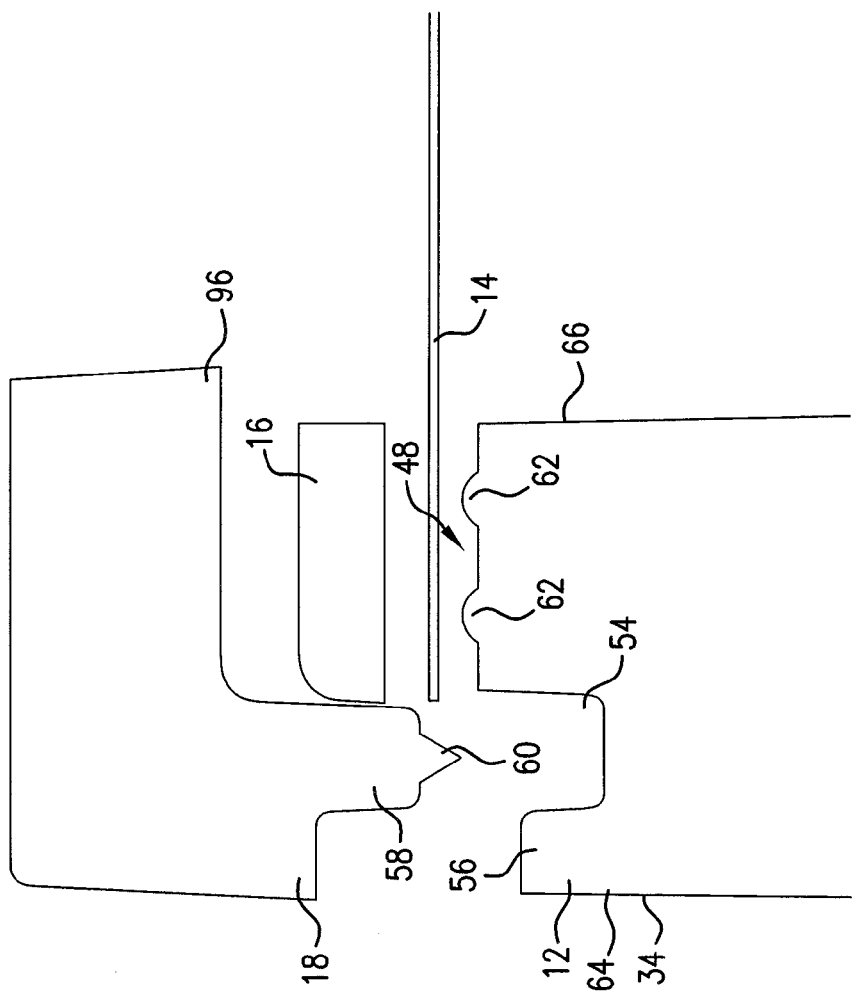
FIG. 8 is an exploded side cross section of the device of FIG. 7, with gripping nubs on the body.

In one embodiment, as shown in cross-section in FIG. 7, and in exploded view in FIG. 8, the peripheral edge 48 of the body 12 comprises an exterior surface 64 (which can be the same as or defined by an end surface 34 or part thereof), an opposed interior surface 66, a recess 54 and a ridge 56. The ridge 56 is located proximal to the outer surface 64 of the body 12 and the recess 54 is positioned between the ridge 56 and the interior surface 66. Both the ridge 56 and recess 54 can extend continuously, or substantially continuously around the peripheral edge 48 (i.e. in one case, extend along at least about 90% of the peripheral edge 48).

As shown in FIG. 8, the body 12 may also have gripping nubs 62 on the peripheral edge 48 of the body 12, proximal to the interior surface 66 and positioned radially inside the recess 54. The gripping nubs 62, when present, provide for further retention of the membrane 14 between the retaining ring 18 and the body 12 by providing a frictional gripping force. However, the nubs 62 are optional and therefore not shown in FIG. 7. In the illustrated embodiment the nubs 62 are shown as relatively small, smoothly curved surfaces which shape can help to minimize tearing of the membrane 14, but the nubs 62 can have any of a wide variety of other shapes and size. Moreover, although two gripping nubs 62 are shown in FIG. 8, it should be understood that more or less gripping nubs 62 can be utilized as desired. The gripping nubs 62, if present, may be continuous or generally continuous around the peripheral edge 48 (i.e. as generally cylindrical portions).

The retaining ring 18, in this embodiment, is generally "L" shaped in cross section and comprises an exterior inner-facing surface 100, an interior inner-facing surface 90, an exterior surface 94, an interior surface 98, and inserting member 58. The inserting member 58 is positioned between and spaced apart from the exterior surface 94 and interior surface 98, and has a size and shape generally corresponding to the recess 54 of the body 12, but may be slightly smaller thereof to allow easy insertion thereof. The inserting member 58 may include a protrusion 60 located at a distal end thereof. The protrusion 60 is configured to contact a bottom surface of the recess 54, and following welding, for example by sonic welding, the protrusion 60 may spread (not shown) and adhere the inserting member 58 to the bottom or other surfaces of the recess 54. If desired, in the embodiment of FIG. 7, or any other embodiment described and shown herein, the position of the protrusion 60 can be reversed such that the protrusion is positioned on the body 12.

FIG. 7 illustrates an conceptual version of the protrusion 60 prior to welding in which the protrusion 60 protrudes into the body 12. A compressive force, pushing the body 12 and retaining ring 18 together, is typically applied during welding to assist in welding and ensure proper attachment. Welding of the protrusion 60 to the recess 54 locks the retaining ring 18 to the body 12 and maintains pressure on the membrane 14 to keep a seal. However, the retaining ring 18/inserting member 58 can be coupled to the body 12/recess 54, and pressure maintained on the membrane 14, by other means besides welding, such as adhesives, press-fit, interference fits, snap-fits, clips, brackets, etc.

After the retaining ring 18 is secured in place, the membrane 14 and gasket 16 are compressed, sandwiched and held between the locked retaining ring 18 and body 12, with the gasket 16 proximate to the retaining ring 18 and the membrane 14 proximate to the body 12 in the illustrated embodiment.

Figure 12:
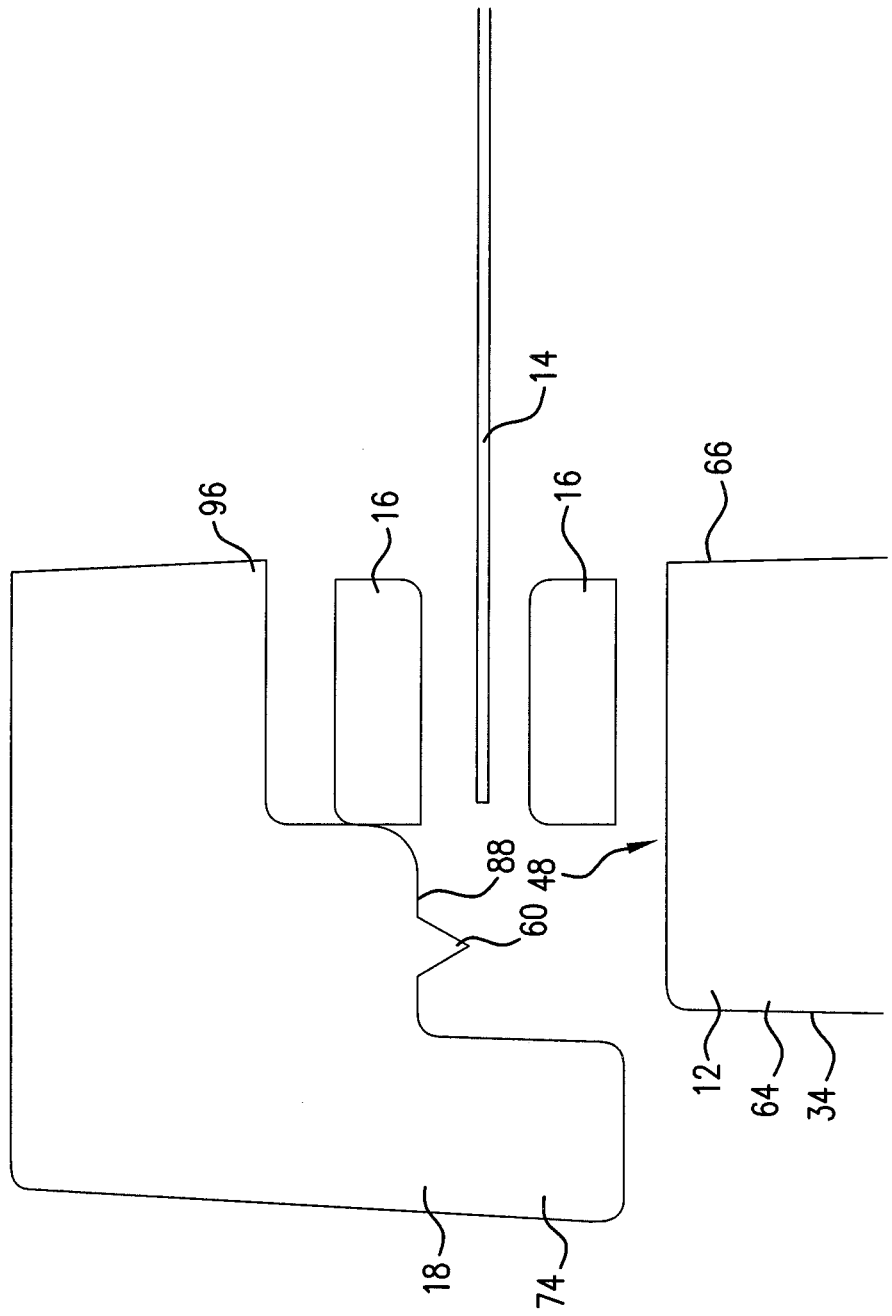
FIG. 12 is an exploded side cross section of the device of FIG. 11.
Figure 13:
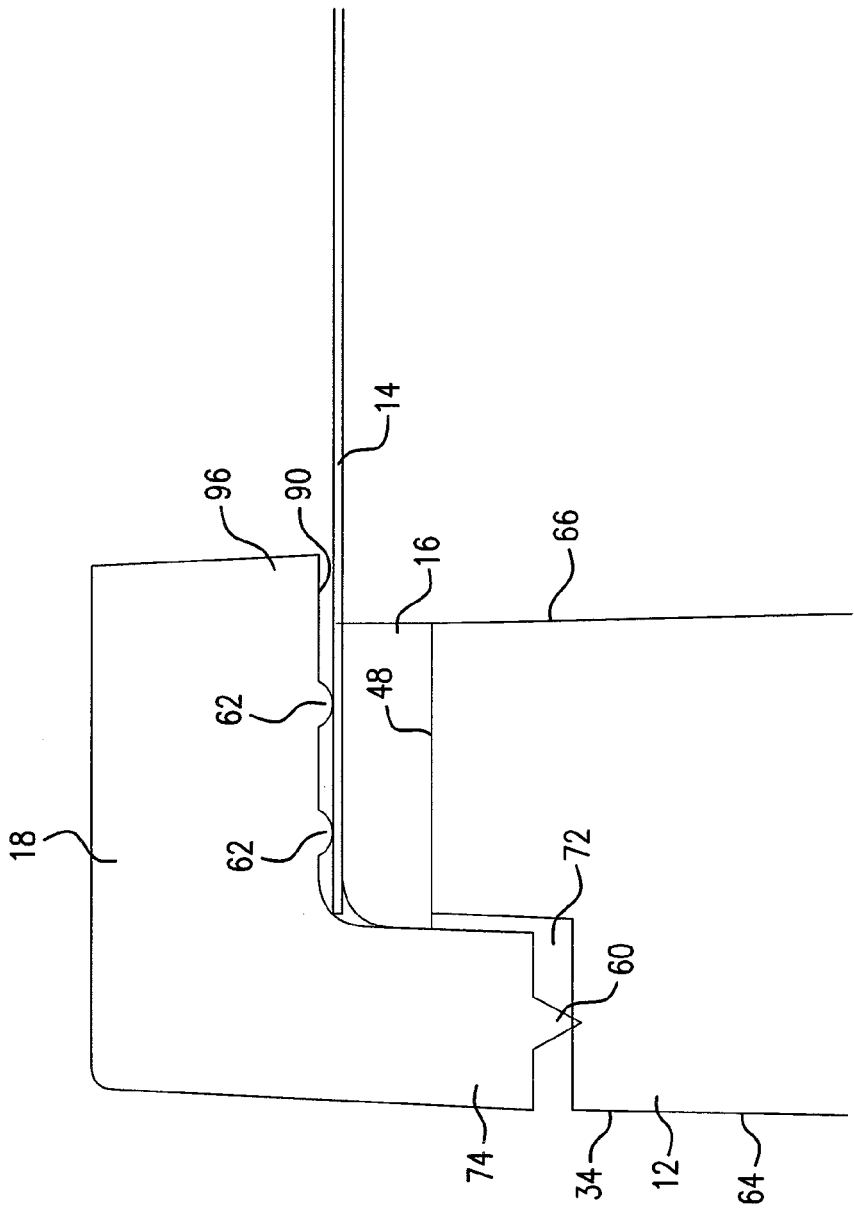
FIG. 13 is a side cross section of another embodiment of the dialysis device, shown in an assembled condition.
Figure 14:
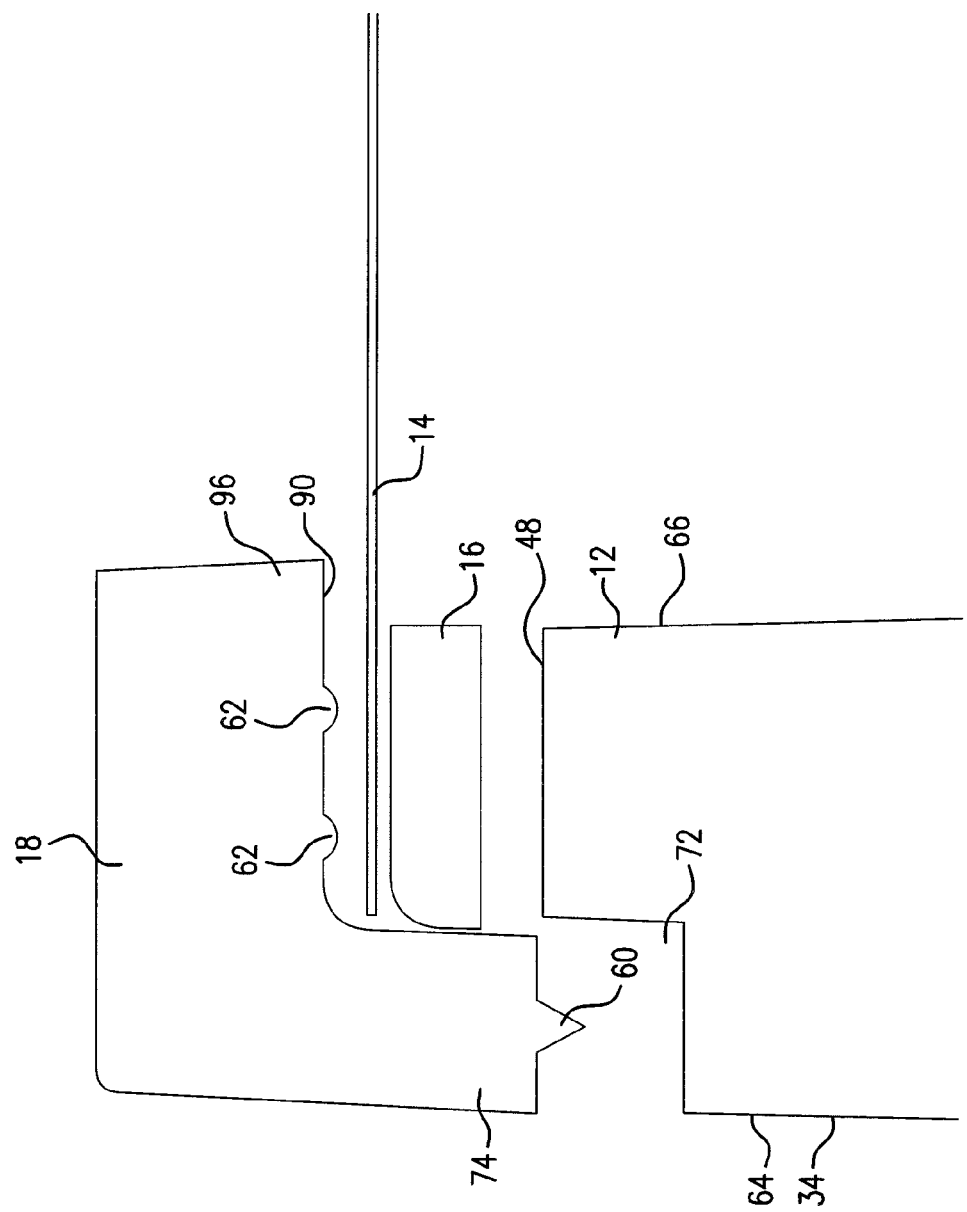
FIG. 14 is an exploded side cross section of the device of FIG. 13.

In an alternate embodiment, the positions of the gasket 16 and membrane 14 may be reversed such that the gasket 16 is proximate to the body 12 and the membrane 14 is proximate to the retaining ring 18 (see, e.g. FIGS. 13 and 14). In this alternate embodiment, the gripping nubs 62 may be present on the interior surface 90 of the retaining ring 18 and in contact with the membrane 14. Alternately, or in addition, the gasket 16 may include nubs 62 that engage the membrane 14. In a further alternate embodiment, two gaskets 16 may be employed such that one gasket 16 is proximate the body 12, the other gasket 16 is proximate to the retaining ring 18, and the membrane 14 is held between the two gaskets 16 (see, e.g. FIGS. 11 and 12). In addition, if desired the position of the inserting member 58 and recess 54 can be reversed such that the inserting member 58 is positioned on the body 12 and the recess 54 is positioned on the retaining ring 58. These alternative arrangements can also be used in the embodiment of FIGS. 7 and 8 as well as the other embodiments described herein.

When the embodiment of FIG. 7 and is in its assembled form, ridge 56 of the base 12 engages exterior surface 100 of the retaining ring 18, or a gap may be left therebetween to ensure proper compression of the membrane 14. Moreover, once secured in place, the inserting member 58 mates with/engages recess 54, and the gasket 16 is positioned against interior surface 90. The interior surface 90 is raised/recessed relative to the exterior surface 100 to account for the extra thickness of the membrane 14, gasket 16 and/or gripping nubs 62. Depending on the number and/or thickness of the gaskets 16 and the thickness of the membrane 14 and nubs 62, the length of the inserting member 58 and dimension other components may need to be adjusted accordingly to ensure proper compression of the membrane 14. As shown in FIGS. 2 and 4, the recess 54 (and therefore ridge 56) and nubs 62 may discontinuously extend around the peripheral edge 48. In this case, the inserting member 58 may also extend discontinuously around the retaining ring 36 in a manner corresponding to the recess 54 (see FIG. 3) so that the retaining ring 18 can be fully seated up against the body 12

The inserting member 58 can fit closely into the recess 54, thereby providing an alignment feature during assembly, ensuring that the retaining ring 18 is properly aligned with respect to the body 12. In addition, in the embodiment alignment of FIGS. 7 and 8, the inserting member 58 is captured on both sides thereof, further ensuring proper alignment. In addition, the retaining ring 18 covers the outer edges of the membrane 14, which can sometimes become wrinkled or stretched after assembly, and there retaining ring 18 provides a pleasing appearance to the dialysis device 10, and can also contain flash from the welding process. In some embodiments, the interior side 98 extends interiorly relative to from the interior surface 66 of the body 12, providing an overhang 96. The overhang 96 can be useful as a shutoff feature to contain overmolding fluid in cases where the gasket 16 is overmolded in the body 12. Moreover, the "L" shape of the retaining ring 18, providing by the inserting member 58, also lends greater stiffness and rigidity to the retaining ring 18 which can be useful, particularly during a welding process in which compressive forces can be applied to the retaining ring 18.

In many cases it is desired to maximize the width of the gasket 16 (i.e. in the left-to-right direction in FIGS. 7 and 8)

while minimizing the width of the retaining ring 18 and/or body 12. In particular, a greater width of the gasket 16 can provide improved sealing, whereas increased width of the retaining ring 18 and/or body 12 can lead to manufacturing difficulties and increase in costs. Thus it may be desired to maximize the ratio of the width of the gasket 16 to the width of the retaining ring 18 and/or body 12. In one case, the dialysis devices has a gasket-to-retaining ring/body width ratio of about least about 0.25 (25%), and at least about 0.50 (50%) in another case.

Figure 9:
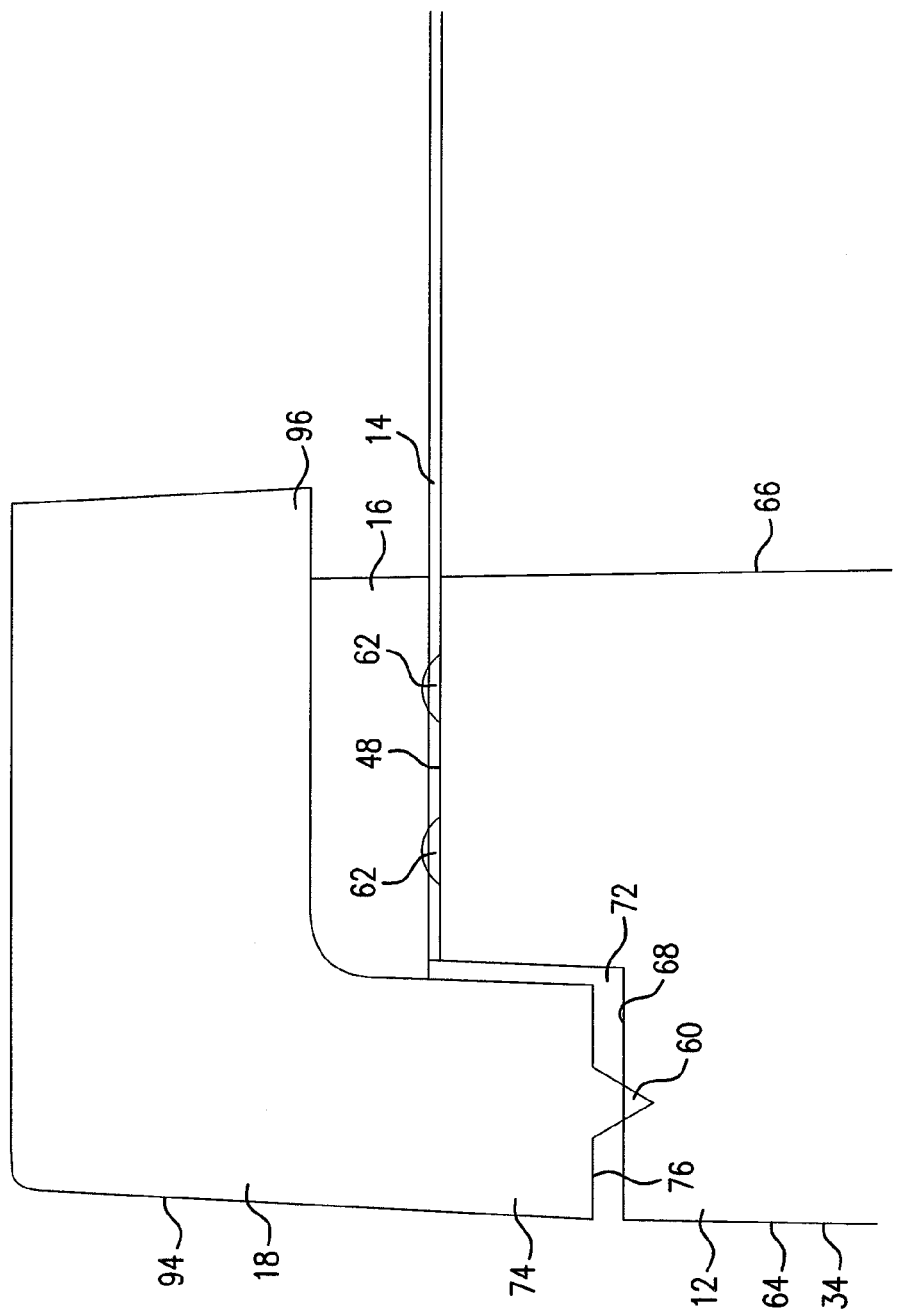
FIG. 9 is a side cross section of another embodiment of the dialysis device, shown in an assembled condition.
Figure 10:
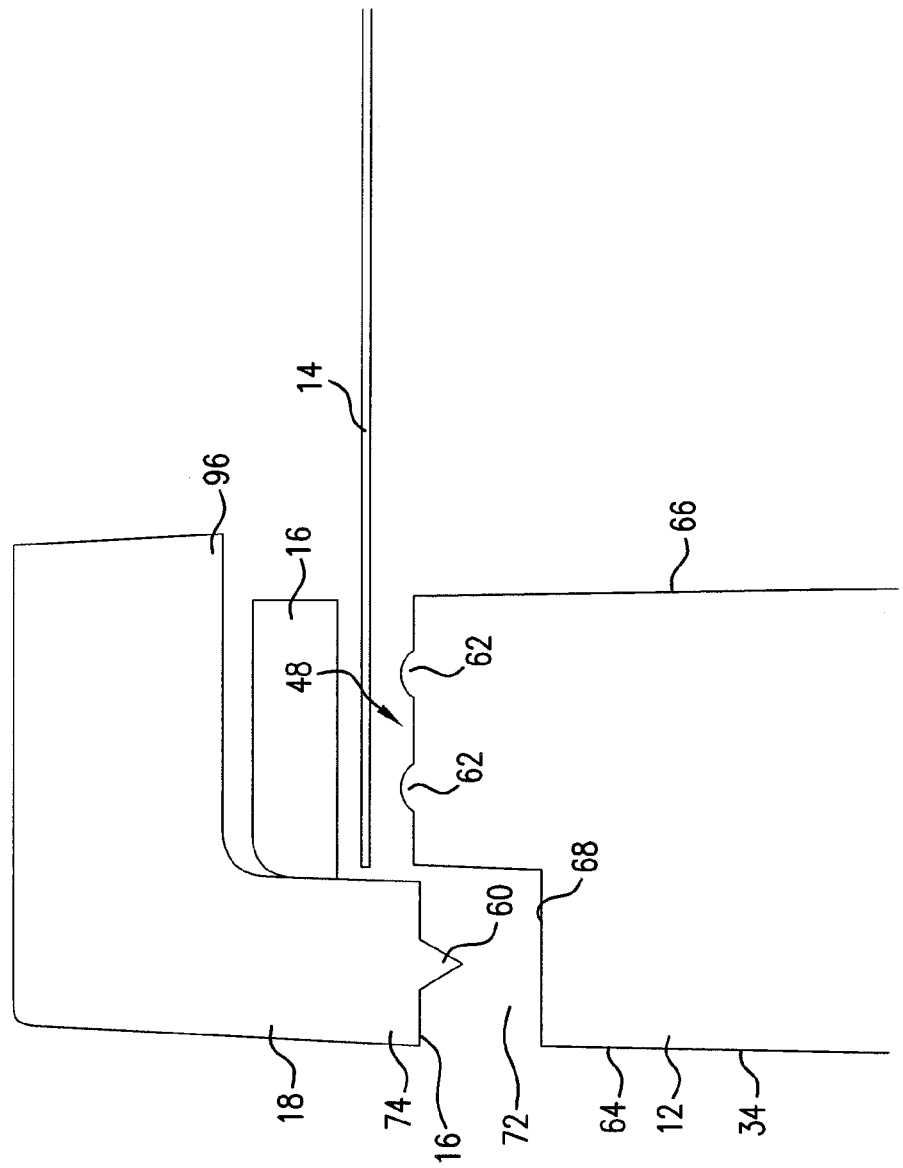
FIG. 10 is an exploded side cross section of the device of FIG. 9.

In another embodiment, as shown in cross-section in FIG. 9, and in exploded view in FIG. 10, the recess 72 is positioned at the outer edge of the body 12, and the body 12 lacks the ridge 56. In this embodiment the inserting member 74 is also positioned at the outer edge of the retaining ring 18. The body 12 may also have membrane gripping nubs 62 on the peripheral edge 48 of the body 12, proximal to the interior surface 66.

The retaining ring 18 is again generally "L" shaped in cross section in this embodiment, comprising the downwardly-extending inserting member 74 which is contiguous with the exterior surface 94 of the retaining ring 18. The inserting member 74 generally corresponds to the dimensions of the cut-out 72 of the body 12. The retaining ring 18 further comprises a protrusion 60 located at a distal end of the inserting member 74 which aids in securing the retaining ring 18 and body 12 as outlined above. In the embodiment of FIGS. 9 and 10, the gasket 16 is positioned between the body 12 and the membrane 14. After assembly the membrane 14 and optional gasket 16 are sandwiched and held between the locked retaining ring 18 and body 12, with the gasket 16 proximate to the retaining ring 18 and the membrane 14 proximate to the body 12.

In one case, the lower surface 68 of the recess 72 is inclined or curved (not shown) toward the interior surface 66. The inclined nature of the lower surface 68 helps to direct any material which has been rendered molten by the welding process away from the exterior surface 64, to prevent the undesirable introduction of melted material or flashing protruding outwardly from the exterior surface 64. In this case the bottom surface 76 of the inserting member 74 can be inclined or shaped in a corresponding manner as the inclined lower surface 68 so that the surfaces 68, 76 can continuously engage each other.

Figure 11:
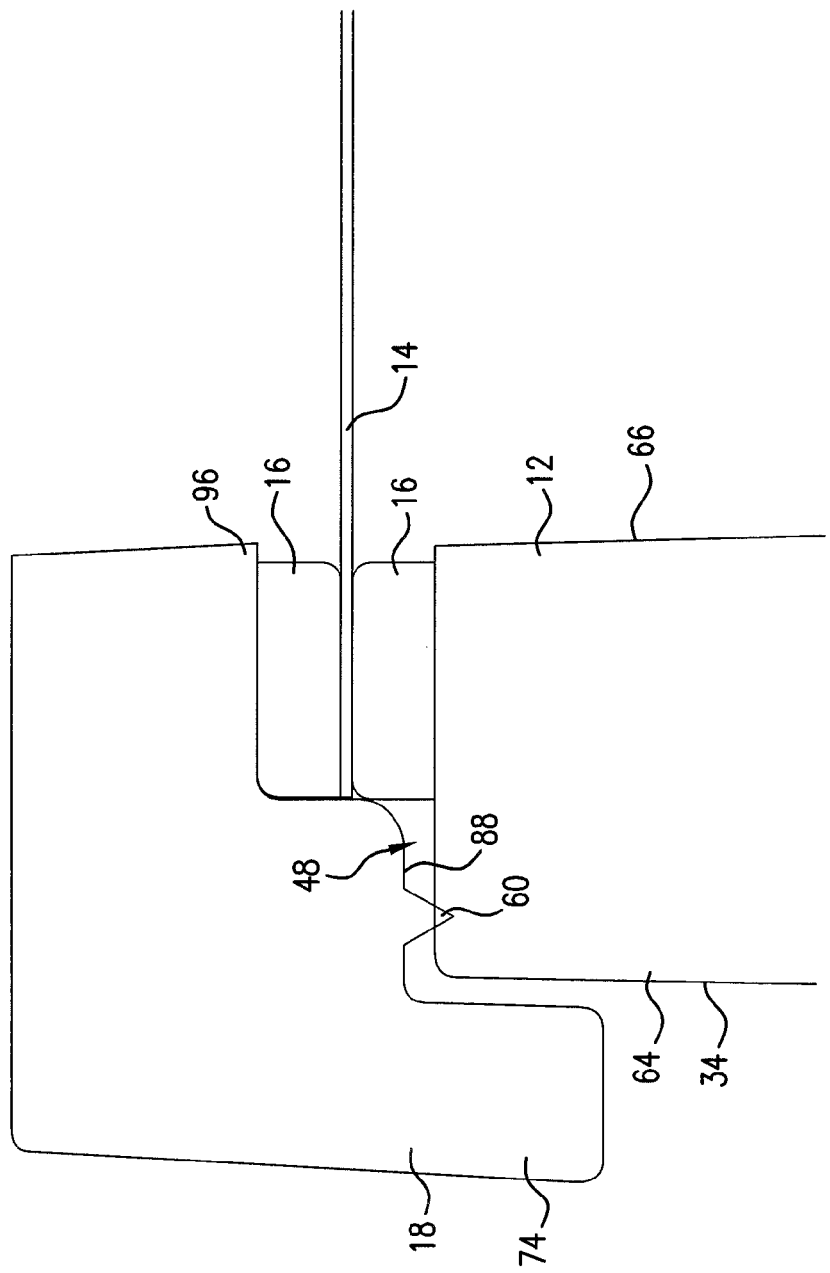
FIG. 11 is a side cross section of another embodiment of the dialysis device, shown in an assembled condition.

In yet another embodiment, as shown in cross-section in FIG. 11, and in exploded view in FIG. 12, the body 12 lacks a recess/cut-out, and the retaining ring 18 has an over-hang portion 74 which fits over the outer edge 34/64 of the body 12. In particular, in this embodiment the body 12 comprises an generally flat peripheral edge 48 extending between the exterior 64 and interior 66 surfaces The interaction between the overhang 74 and the exterior surface 64 helps to properly position the retaining ring 18. In this particular embodiment a pair of gaskets 16 are utilized to hold the membrane 14 therebetween. The lower gasket 16 is disposed on the peripheral edge 48 of the body 12, proximal to the interior surface 66. In one embodiment, the lower gasket 16 is set back from the plane defined by interior surface 66 of the body 12 such that the lower gasket 16 is recessed from view. Alternately, the gasket(s) 16 may be omitted and the body 12 and/or retaining ring 18 may have gripping nubs. Further alternately, the gasket(s) 16 may include gripping nubs thereon. A gasket 16 may be more pliable and provide a better sealing surface than the body 12/retaining ring 18, and therefore the use of a gasket 16 on either side of the membrane 14 may provide improve sealing. The retaining ring 18 further comprises a protrusion 60 located on a first interior horizontal surface 88, which in the assembled state, is generally parallel with the peripheral edge 48 of the body 12. The protrusion 60 is spaced away (inwardly) from the inserting member 74 and is used to couple the retaining ring 18 to the body 12.

FIGS. 13 and 14 illustrate an embodiment similar to FIGS. 9 and 10, except the position of the gasket 16 and membrane 14 are reversed, and the retaining ring 18 include gripping nubs 62.

As shown in FIGS. 1, 2 and 6, the retaining ring 18 can include gripping tabs 36 integrally formed therewith, positioned at or adjacent to corners thereof, which can facilitate handling the dialysis device 10 while minimizing contact with the membrane 14. The retaining ring 18 may further include a labeling/identification portion 38 positioned along a bottom edge thereof in the illustrated embodiment. Any number of gripping tabs 36 and/or labeling/identification portion 38 may utilized, and they can be placed at nearly any position around the perimeter of the retaining ring 18. The gripping means 36 and labeling/identification portion 38, when present, may have smoothed edges, particularly for those edges facing the membrane 14, to minimize harm or tearing of the membrane 14.

To use the device 10, a fluid or liquid sample is placed in the interior volume 40 of the via access opening 24. If not filed to the desired amount, the dialysis device 10 may be squeezed or compressed until the desired amount of air remains in the dialysis device 10. The cap 17 or other closure device is then secured to the access opening 24 of the dialysis device 10, sealing the sample in the dialysis device 10 along with any trapped air. The dialysis device 10 is then placed into a vessel containing liquid dialysate. The trapped air in the device 10 may impart the desired buoyancy to the dialysis device 10, ensuring proper orientation of the dialysis device 10 in the dialysate. Alternately, or in addition, a float or buoyancy device can be attached to the neck 25 or other portion of the dialysis device 10. Relatively large molecules in the sample, such as proteins, which are larger than pores in the membrane 14 are retained within the interior volume 40 of the dialysis device 10. In contrast, relatively small molecules, such as buffer molecules, within the interior volume 40 exchange by diffusion with the buffer molecules in the dialysate. The dialysis device 10 containing the sample is maintained in the dialysate for a desired amount of time.

In one embodiment, after a few hours of dialysis, the sample may show at least a 90% reduction in small molecules. If desired, the dialysis procedure can be enhanced by removing the dialysate and replacing with a fresh dialysate. Replacing the dialysate in this manner, and allowing sufficient time for dialysis, may, in one embodiment, allow well over 99% of the targeted small molecules to be removed from the sample. In one embodiment, the sample has a volume of between about 125 and about 250 milliliters, although the sample volume and size of the device 10 can be varied as desired. Following dialysis of the sample in the dialysis device, the sample can be removed from the dialysis device 10 by pouring and/or pipetting the sample through the access opening 24 from the dialysis device 10. In some cases, the cap 17 may include a septum that may allow a needle to penetrate therethrough to remove portions of the sample from, or add portions of the sample to, the inner volume 40.

The described dialysis device provides an efficient and cost effective means for sealing the membrane 14 to the body 12, which is easy to assemble and provides a robust connection.

Although the invention is shown and described with respect to certain embodiments, it should be clear that modifications and variations will be apparent to those skilled in the art upon reading the specification, and the present invention includes all such modifications and variations.

What is claimed is:

1. A dialysis device comprising
   a body at least partially defining an inner volume and having an access opening in fluid communication with the inner volume, the body defining first and second peripheral edges on generally opposite sides thereof;
   a first and a second retaining ring disposed about each of the first and second peripheral edges, respectively;
   a first gasket positioned between the first retaining ring and the first peripheral edge, and a second gasket positioned between the second retaining ring and the second peripheral edge;
   a first dialysis membrane positioned between the first peripheral edge and the first retaining ring; and
   a second dialysis membrane positioned between the second peripheral edges and the second retaining ring, wherein the dialysis device is configured to receive a sample in the inner volume to enable dialysis of the sample across the first and second membranes.

2. The dialysis device of claim 1 wherein the first peripheral edge defines a first major opening of the body and the second peripheral edge defines second major opening of the body, and wherein the first dialysis membrane entirely covers the first major opening and the second peripheral edge entirely covers the second major opening.

3. The dialysis device of claim 1 wherein the body has a width extending in a lateral direction thereof across a peripheral edge, and wherein each gasket has a width extending in the lateral direction that is at least about 25% of the width of the body.

4. The dialysis device of claim 1 wherein the first dialysis membrane is positioned between the first gasket and the first peripheral edge, and the second dialysis membrane is positioned between the second gasket and the second peripheral edge.

5. The dialysis device of claim 1 wherein at least one of the body and one of the retaining rings has an inserting member configured to fit into a recess, or to overhang an outer edge, of the other of the body or the one of the retaining rings.

6. The dialysis device of claim 1 wherein at least one of the retaining rings has an inserting member configured to fit into a corresponding recess, or to overhang an outer edge, of the body.

7. The dialysis device of claim 6 wherein the inserting member is spaced away from the outer edge of the associated retaining ring.

8. The dialysis device of claim 6 wherein the inserting member is positioned at the outer edge of the associated retaining ring.

9. The dialysis device of claim 6 wherein the body has a recess that closely receives the inserting member therein.

10. The dialysis device of claim 9 wherein the inserting member is welded to the recess.

11. The dialysis device of claim 9 wherein the retaining ring is coupled to the body at a position spaced away from the inserting member.

12. The dialysis device of claim 9 wherein the recess is spaced away from the outer edge of the body.

13. The dialysis device of claim 9 wherein the recess is positioned at the outer edge of the body.

14. The dialysis device of claim 9 wherein a lateral surface of the recess is shaped to direct molten materials away from the outer edge of the body when the inserting member is welded to the recess.

15. The dialysis device of claim 6 wherein the inserting member extends around generally an entire peripheral edge of the associated retaining ring.

16. The dialysis device of claim 1 wherein the device is configured such that a sample positioned within the inner volume is fluidly isolated from any surrounding fluid except by dialysis through the membranes, and wherein each membrane is a semi-permeable dialysis membrane.

17. The dialysis device of claim 1 further comprising gripping nubs positioned adjacent to at least one membrane between one of said retaining rings and said body for securing the at least one membrane in place.

18. A dialysis device comprising
   a body at least partially defining an inner volume, the body defining first and second openings on generally opposite sides thereof;
   a first retaining ring extending about the first opening and coupled to the body;
   a second retaining ring extending about the second opening and coupled to the body;
   a first gasket positioned between the first retaining ring and the body;
   a second gasket positioned between the second retaining ring and the body;
   a first dialysis membrane extending over the first opening and positioned between the body and the first retaining ring; and
   a second dialysis membrane extending over the second opening and positioned between the body and the second retaining ring, wherein the dialysis device is configured to receive a sample therein to enable dialysis of the sample across the first and second membranes.

19. A method for using a dialysis device comprising
   accessing a dialysis device having a body defining first and second peripheral edges on generally opposite sides thereof, a first and a second retaining ring disposed about each of the first and second peripheral edges, respectively, a first gasket positioned between the first retaining ring and the first peripheral edge, a second gasket positioned between the second retaining ring and the second peripheral edge, a first dialysis membrane positioned between the first peripheral edge and the first retaining ring, and a second dialysis membrane positioned between the second peripheral edges and the second retaining ring;
   placing a sample in the dialysis device such that the sample is in contact with both membranes; and
   placing the dialysis device in contact with a buffer such that the buffer is contact with both membranes to enable dialysis of the sample with respect to the buffer across the membranes.

20. A dialysis device comprising
   a body at least partially defining an inner volume and having a peripheral edge on one side thereof;
   a retaining ring extending about the peripheral edge;
   a gasket positioned between the retaining ring and the peripheral edge; and
   a dialysis membrane positioned between the peripheral edge and the retaining ring, wherein the dialysis device is configured to receive a sample in the inner volume to enable dialysis of the sample across the membrane.

* * * * *